(12) United States Patent
Wright et al.

(10) Patent No.: US 6,387,373 B1
(45) Date of Patent: *May 14, 2002

(54) VACCINES CONTAINING PAUCILSMELLAR LIPID VESICLES AS IMMUNOLOGICAL ADJUVANTS

(75) Inventors: D. Craig Wright, Gaithersburg, MD (US); Donald F. H. Wallach, Geneva (CH)

(73) Assignee: Novavax, Inc., Rockville, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/840,034

(22) Filed: Apr. 24, 1997

Related U.S. Application Data (63) Continuation-in-part of application No. 08/201,346, filed on Feb. 24, 1994, now abandoned, and a continuation-in-part of application No. 08/005,008, filed on Jan. 15, 1993, now abandoned.

(51) Int. Cl.[7] ...................... A61K 39/00; A61K 39/145; A61K 39/155; A61K 9/127
(52) U.S. Cl. ................ 424/192.1; 424/450; 424/184.1; 424/211.1; 424/209.1; 424/210.1; 424/420
(58) Field of Search .............................. 424/450, 184.1, 424/420, 210.1, 209.1, 211.1, 192.1

(56) References Cited

U.S. PATENT DOCUMENTS

| | | | | |
|---|---|---|---|---|
| 5,147,723 A | * | 9/1992 | Wallach |
| 5,547,677 A | * | 8/1996 | Wright |
| 5,549,901 A | * | 8/1996 | Wright |
| 5,561,062 A | * | 10/1996 | Varanelli et al. |
| 5,618,840 A | * | 4/1997 | Wright |
| 5,628,936 A | * | 5/1997 | Wallach |
| 5,629,021 A | * | 5/1997 | Wright |
| 5,665,380 A | * | 9/1997 | Wallach et al. |
| 5,683,702 A | * | 11/1997 | Becker et al. |
| 5,700,679 A | * | 12/1997 | Wright |
| 5,730,989 A | * | 3/1998 | Wright |
| 5,762,939 A | * | 6/1998 | Smith et al. |
| 5,795,582 A | * | 8/1998 | Wright |
| 5,827,531 A | * | 10/1998 | Morrison et al. |
| 5,858,368 A | * | 1/1999 | Smith et al. |

* cited by examiner

*Primary Examiner*—Nita Minnifield
(74) *Attorney, Agent, or Firm*—Lahive & Cockfield, LLP (57) ABSTRACT

The present invention features an adjuvanted vaccine, and methods for preparing an adjuvanted vaccine, preferably for immunizing against influenza, where the adjuvant is a lipid vesicle, and preferably is a nonphospholipid, paucilamellar lipid vesicle. The antigen may be encapsulated in the central cavity of the adjuvant, or mixed in solution with the adjuvant. Moreover, the adjuvant may carry a secondary adjuvant to further improve the immune response.

8 Claims, 7 Drawing Sheets

| Influenza A/Beijing 32/92 H$_3$N$_2$ Subunit Nonfusogenic Novasome® Vaccine | | | Influenza A/Beij

| Influenza A/Beijing 32/92 H$_3$N$_2$ Subunit Nonfusogenic Novasome® Vaccine | | | Influenza A/Beijing 32/92 H$_3$N$_2$ Subunit Vaccine | | |
|---|---|---|---|---|---|
| Rat # | HAI Titer | ELISA Titer | R

| Group No. | Immunogen | Day 7 | Day 14 | Day 28 | Day 37 | Day 44 | Day 58 |
|---|---|---|---|---|---|---|---|
| 1 | H3N2 Vaccine in B7 Novasomes® Adjuvant | 14,848 | 104,000 | 160,000 | 281,600 | 409,600 | 332,800 |
| 2 | H3N2 Vaccine in B5 Novasomes® Adjuvant | 6,816 | 26,400 | 39,600 | 108,600 | 185,600 | 184,000 |
| 3 | H3N2 Vaccine | 352 | 2666 | 5,227 | 7,253 | 7,680 | 7,680 |

*FIG. 6*

| Vaccine | Reciprocal GMT ELISA | HI (GMT) | Folds increase over *Influenza* vaccine alone (HI GMT) |
| --- | --- | --- | --- |
| Influenza H3N2 Vaccine | 262 | 254 | |
| Influenza H3N2 Vaccine in B5COASE Novasomes® | 8,086 | 1,595 | 6.3 |

*FIG. 7*

VACCINES CONTAINING PAUCILSMELLAR LIPID VESICLES AS IMMUNOLOGICAL ADJUVANTS

REFERENCE TO RELATED APPLICATIONS

This application is a continuation-in-part of U.S. patent application Ser. No. 08/005,008 filed Jan. 15, 1993, entitled Method of Inhibiting Viral Reproduction, now abandoned and of Ser. No. 08/201,346, filed Feb. 24, 1994, entitled Vaccines Containing Paucilamellar Lipid Vesicles as Immunological Adjuvants, now abandoned the disclosures of which are incorporated herein by reference.

BACKGROUND OF THE INVENTION

The present invention relates to an adjuvanted vaccine, where lipid vesicles, particularly nonphospholipid lipid vesicles, serve as the adjuvant, together with methods of preparing the vaccine. Immunological adjuvants are the component of the vaccine which augment the immune response to the antigen. Immunological adjuvants function by, inter alia, attracting macrophages to the antigen and then to present that antigen to the regional lymph nodes and initiate an effective antigenic response. Adjuvants may also act as carriers themselves for the antigen. Many of the known immunological adjuvants, such as Freund's complete adjuvant, alum, aluminum hydroxides, and Freund's incomplete adjuvant, while effective at initiating the antigenic response, produce undesirable reactions in humans, such as inflammation at the point of injection. These side effects prevent use of such adjuvants in humans, and have led to the search for alternative immunological adjuvants.

Lipid vesicles are substantially spherical structures made of amphiphiles, e.g., surfactants or phospholipids. The lipids of these spherical vesicles are generally organized in the form of lipid bilayers, e.g., multiple onion-like shells of lipid bilayers which encompass an aqueous volume between the bilayers. Certain types of lipid vesicles have an unstructured central cavity which can be used to encapsulate and transport a variety of materials. Paucilamellar lipid vesicles, for example, have 2–10 peripheral bilayers surrounding a large, unstructured central cavity.

Until recently, liposome technology has been concerned mostly with vesicles composed of phospholipids. This is primarily because phospholipids are the principal structural components of natural membranes and, accordingly, lipid vesicles have been used as a model system for studying natural membranes. However, there are a number of problems associated with using phospholipids as synthetic membranes. Phospholipid liposomes placed in an in vivo environment are rapidly degraded. Moreover, phospholipids are labile and expensive to purify or synthesize. In addition, classic phospholipid liposomes are in the form of multilamellar as opposed to paucilamellar vesicles and have poor carrying capacities, especially for lipophilic materials, and have poor shelf lives unless lyophilized in the dark with antioxidants. Finally, phospholipids degrade too rapidly in vivo for most pharmaceutical or vaccine applications.

For these reasons, there is increasing interest in liposomes made of commercially available nonphospholipid amphiphiles (see, e.g.,U.S. Pat. No. 4,217,344, U.S. Pat. No. 4,917,951, and U.S. Pat. No. 4,911,928). These molecules have a hydrophilic head group attached to a hydrophobic "tail" and are derived from long chain fatty acids, long chain alcohols and their derivatives, long chain amines, and polyol sphingo- and glycerolipids. Commercially available amphiphile surfactants include, for example, the BRIJ™ family of polyoxyethylene fatty ethers, the SPAN sorbitan fatty acid esters, and the TWEEN polyoxyethylene derivatives of sorbitan fatty acid esters, all available from ICI Americas, Inc. of Wilmington, Del. Paucilamellar vesicles containing such amphiphiles provide a high carrying capacity for water-soluble and water immiscible substances. The high capacity for water immiscible substances represents a unique advantage over classical phospholipid multilamellar liposomes.

Paucilamellar lipid vesicles may include a wide variety of phospholipids and nonphospholipid surfactants as their primary structural material. Paucilamellar lipid vesicles are substantially spherical structures made of materials having a high lipid content, preferably from nonphospholipid materials, which are organized in the form of lipid bilayers. The two to ten peripheral bilayers encapsulate an aqueous volume which is interspersed between the lipid bilayers and may also be encapsulated in the amorphous central cavity. Alternatively, the amorphous central cavity may be substantially filled with a water immiscible material, such as an oil or wax. Paucilamellar lipid vesicles have advantages as transport vehicles because large unstructured central cavity is easily adaptable for transport of large quantities of aqueous or oleaginous materials.

As described above, to stimulate a specific immune response, two components are required, namely the antigen or immunologicaly specific substance, and an adjuvant, the component augmenting the immune response to the antigen. Conventional adjuvants can serve as vehicles for the antigen, and as nonspecific immunological stimulants. The inventors have discovered that paucilamellar lipid vesicles are effective immunological adjuvants.

Accordingly, it is an object of the invention to provide an adjuvanted vaccine for immunizing against influenza, where paucilamellar lipid vesicles are the adjuvant.

Another object of the invention is to provide an adjuvanted vaccine to stimulate an immune response in a mammal, where the adjuvant is a nonphospholipid paucilamellar lipid vesicle which acts as a non-specific immune stimulator, an adjuvant/antigen carrier, or as a carrier of chemical adjuvants.

A further object of the invention is to provide a method of preparing adjuvanted vaccines useful in treating viral infections in mammals.

These and other objects and features of the invention will be apparent from the following description and from the claims.

SUMMARY OF THE INVENTION

The present invention features an adjuvanted vaccine, and methods for preparing an adjuvanted vaccine, preferably for immunizing against influenza, where the adjuvant is a lipid vesicle, and preferably is a nonphospholipid, paucilamellar lipid vesicle. The antigen may be encapsulated in the central cavity of the adjuvant, or mixed in solution with the adjuvant. Moreover, the adjuvant may carry a secondary adjuvant to further improve the immune response.

The antigen is preferably an influenza antigen and may comprise a formalin-inactivated whole virus, formalin-inactivated viral subunits, or an antigen produced by recombinant DNA techniques.

In one embodiment, the adjuvanted flu vaccine is prepared whereby the paucilamellar lipid vesicles, the preferred adjuvant, are prepared separately, and the adjuvant is then intermixed with the antigen. Alternatively, an adjuvanted vaccine can be prepared by forming paucilamellar lipid vesicles encapsulating the antigen.

The adjuvant in one embodiment of the invention is a paucilamellar lipid vesicle having about two to ten bilayers arranged in the form of substantially spherical shells separated by aqueous layers surrounding a large amorphous central cavity free of lipid bilayers. The lipid bilayers preferably have as their primary lipid component one or more of a the following nonphospholipid materials: polyoxyethylene fatty acid esters, polyoxyethylene fatty acid ethers, polyoxyethylene sorbitan esters, polyoxyethylene glyceryl mono- and diesters, glyceryl mono-and distearate, sucrose distearate, propylene glycol stearate, long chain acyl hexosamides, long chain acyl amino acid amides, long chain acyl amides, glyceryl mono-and diesters, dimethyl acyl amines, $C_{12}$–$C_{20}$ fatty alcohols, $C_{12}$–$C_{20}$ glycol monoesters, $C_{12}$–$C_{20}$ fatty acids, and mixtures thereof. More preferably, this mixture further contains at least one sterol selected from the group consisting of cholesterol, cholesterol derivatives, hydrocortisone, phytosterol, and mixtures thereof, a charge producing agent, and any lipid soluble or water soluble materials to be incorporated into the vesicles.

The vesicles of the present invention have a central cavity, carrying either water soluble materials or a water-immiscible oily solution, which can be used to encapsulate the antigen. The water-immiscible oily solution is made of materials which are both water immiscible and immiscible in the lipids used to form the bilayers. The water immiscible oily material found the amorphous central cavity may comprise soybean oil, squalene oil, squalane oil, sesame oil, olive oil, canola oil, corn oil, rapeseed oil, safflower oil, sunflower oil, fish oils, petrolatum, avocado oil, triglyceride oils and fats, flavor oils, water insoluble vitamins, and mixtures thereof. These materials provide pharmacological benefits in addition to the benefits caused by the use of the particular lipids which form the bilayers.

The invention further features methods of producing adjuvanted vaccines. The adjuvant may comprise water or oil filled vesicles, e.g., vesicles having their amorphous central cavities filled with a water-immiscible oily solution, and these may be formed using either the "hot loading" technique disclosed in U.S. Pat. No. 4,911,928 or the "cold loading" technique described in the U.S. Pat. No. 5,160,669, the disclosures of which are incorporated herein by reference. In either case, a lipid phase is formed by blending the nonphospholipid material, along with any sterols or lipophilic materials to be incorporated into the lipid bilayers, to form a homogenous lipid phase. In the "hot loading" technique, any water-immiscible oily material to be encapsulated in the vesicles is blended in the already formed lipid phase, forming a lipophilic phase. Oil-soluble or oil-suspendable antigens to be encapsulated within the vesicles are first dispersed in the oil. The term "dispersed" as used herein includes dissolution or forming a suspension or colloid to yield a flowable phase.

Once a lipophilic phase is made, it is blended with an aqueous phase (e.g., water, saline, or any other aqueous solution which will be used to hydrate the lipids), which may also contain an antigen, under shear mixing conditions to form the adjuvant. "Shear mixing conditions", as used herein, means a shear equivalent to a relative flow of 5–50 m/s through a 1 mm orifice.

In the alternative, the vaccine can be incorporated into the amorphous central cavity of the adjuvant by the "cold-loading" technique described in U.S. Pat. No. 5,160,669 to Wallach et al.

The scope and application of the invention will be apparent from the following detailed description.

DETAILED DESCRIPTION OF THE INVENTION

The present invention involves use of paucilamellar lipid vesicles as adjuvants in a vaccine to increase the antigenic response in a mammal inoculated with the vaccine. The vesicles are preferably nonphospholipid vesicles, and the antigen is preferably an influenza antigen.

Paucilamellar lipid vesicles act to stimulate the immune response several ways, as non-specific stimulators, as carriers for the antigen, as carriers of additional adjuvants, and combinations thereof. Paucilamellar lipid vesicles act as non-specific immune stimulators when, for example, a vaccine is prepared by intermixing the antigen with the pre-formed vesicles such that the antigen remains extracellular to the vesicles. By encapsulating an antigen within the central cavity of the vesicle, the vesicle acts both as an immune stimulator and a carrier for the antigen. Alternatively, the vesicles can act as carriers for the antigen by filing with the antigen, as is described in U.S. Pat. application Ser. No. 08/005,008 filed Jan. 15, 1993, entitled *Method of Inhibiting Viral Reproduction*, of which this application is a continuation-in-part. In this embodiment, when the antigen, there an enveloped virus, is mixed with the paucilamellar lipid vesicles, the virus and adjuvant fuse, denaturing the nucleic acid and inactivating the virus. The inactivated virus/adjuvant hybrid is then useful as a vaccine. Moreover, the vesicle can serve to carry additional adjuvants within the central cavity or between the bilayers.

The following Examples will clearly illustrate the efficacy of the invention.

Example 1

Figure 1:
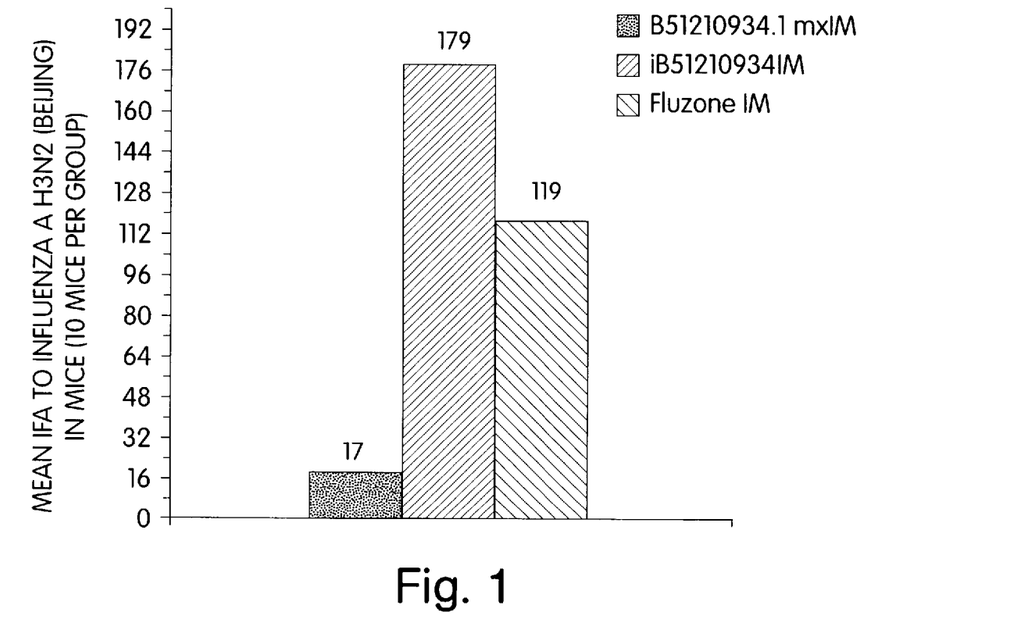
FIG. 1 is a graph of the mean Indirect Fluoresent Assay Day results in mice at Day 42 following one inoculation with adjuvanted influenza A vaccines.
Figure 2:
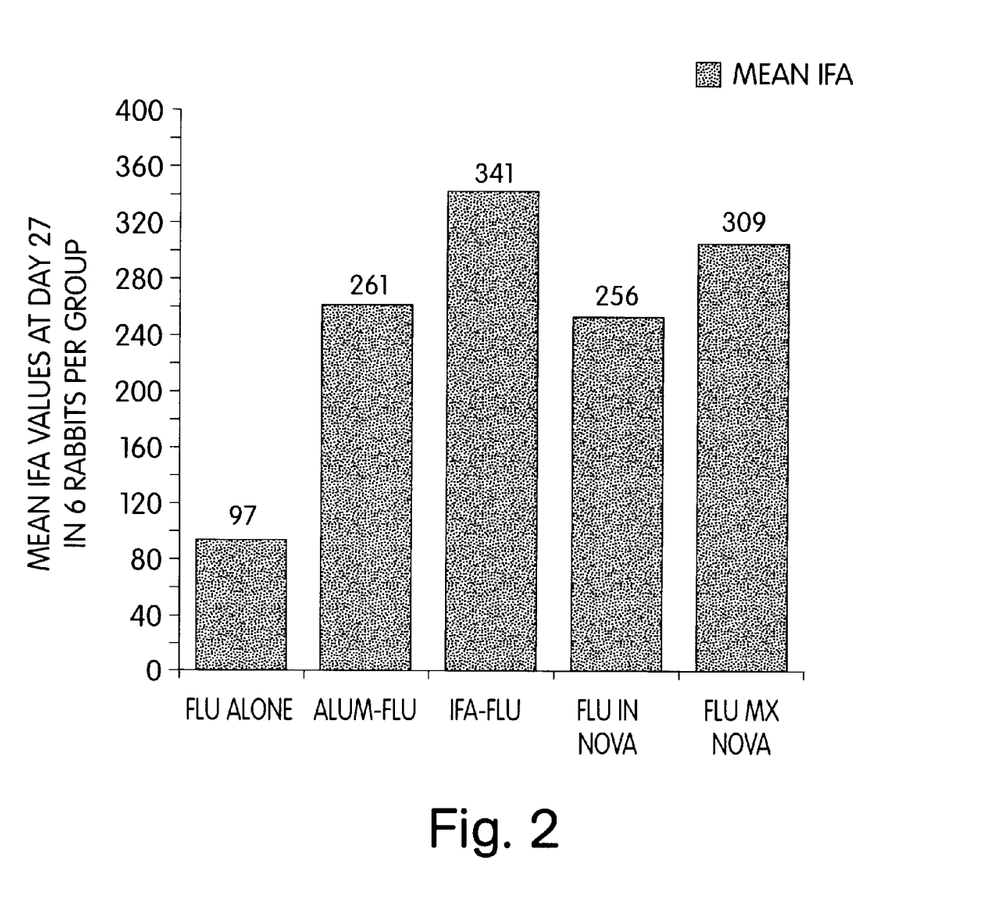
FIG. 2 illustrates the mean Indirect Fluoresent Assay Day values in rabbits at Day 27 following two inoculations with adjuvanted influenza A vaccines.
Figure 3:
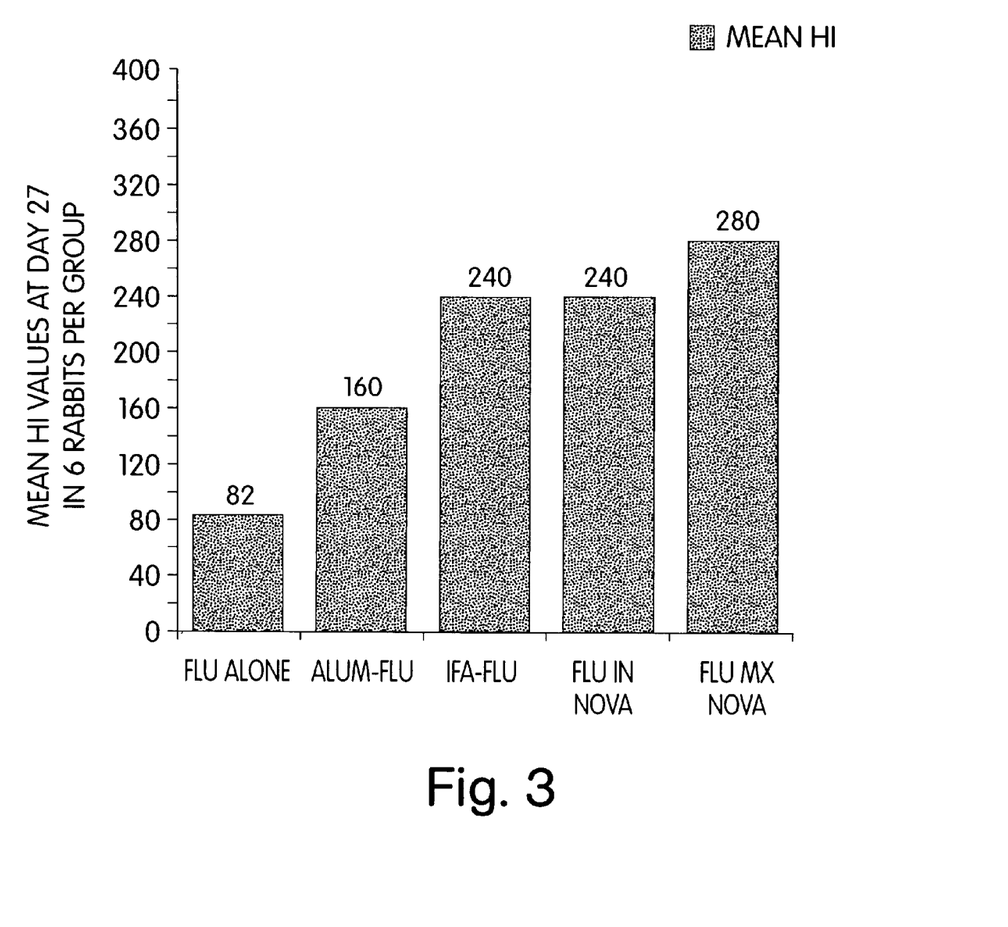
FIG. 3 illustrates the mean Hemagglutination Inhibition Assay Day values in rabbits at Day 27 following two inoculations with adjuvanted influenza A vaccines.
Figure 4:
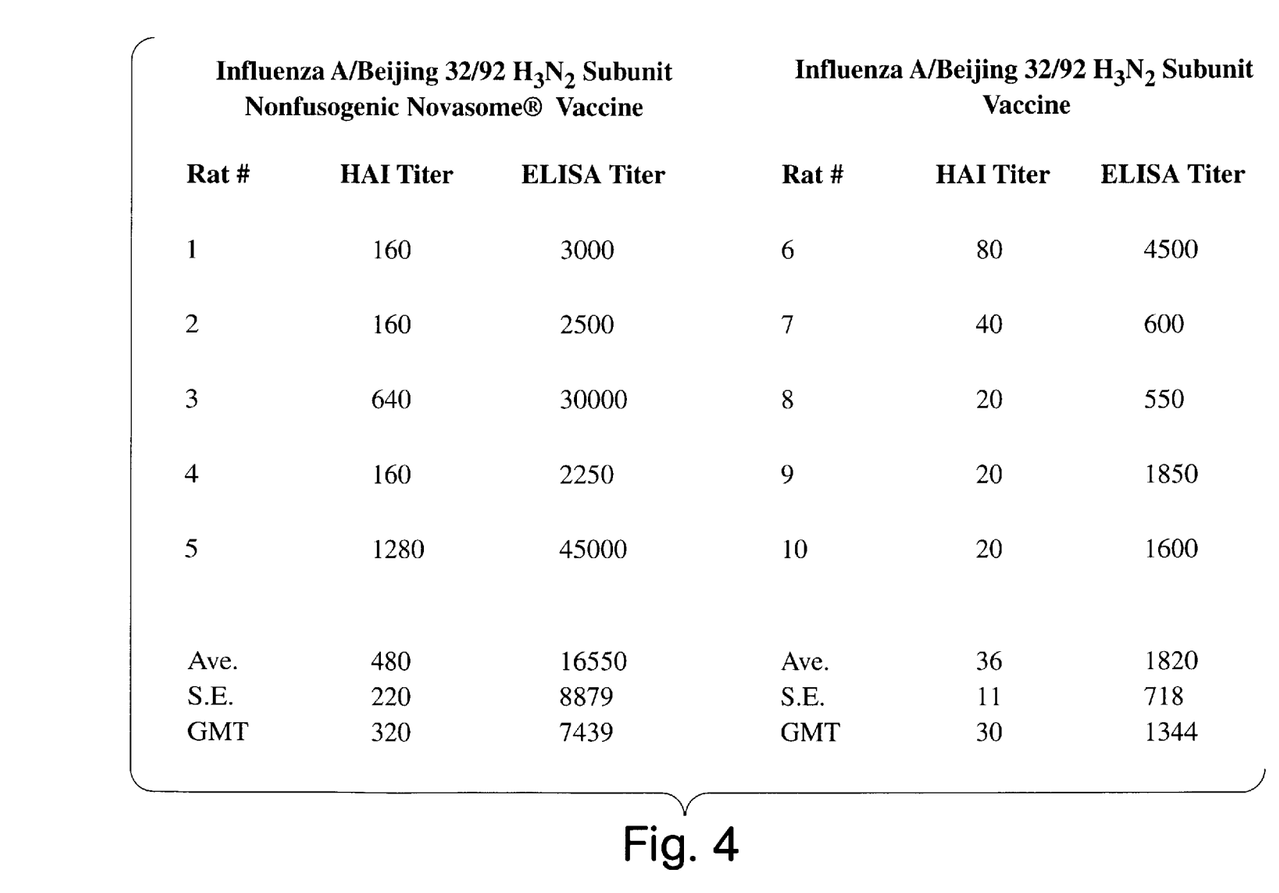
FIG. 4 illustrates the Hemagglutination Inhibition Assay Enzyme-Linked Immunsorbent and results in rats at Day 69 following the assay inoculations with an adjuvanted and non-adjuvanted influenza A vaccine.
Figure 5:
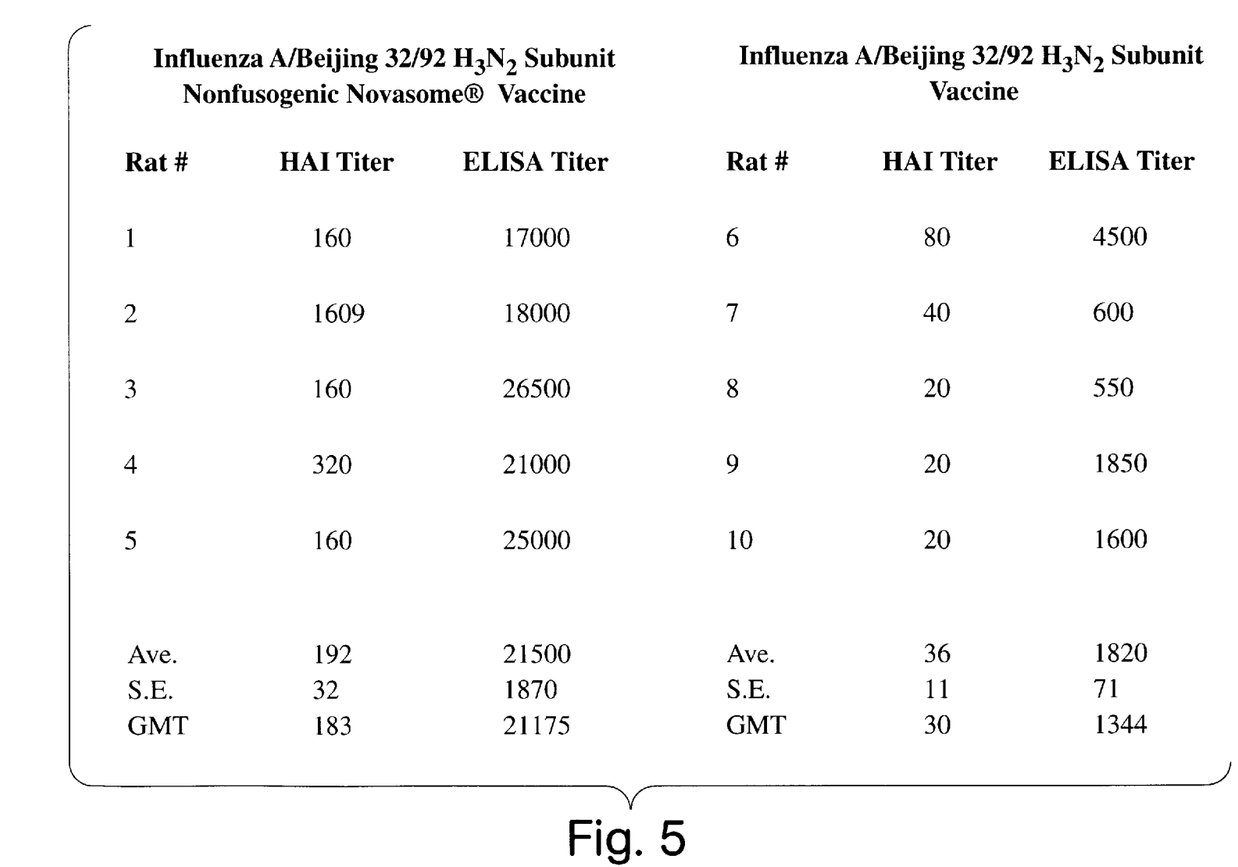
FIG. 5 illustrates the Hemagglutination Inhibition Assay Enzyme-Linked Immunabsorbent and results in rats at Day 69 or 71 following assay two inoculations with an adjuvanted influenza vaccine and a non-adjuvanted influenza vaccine.
Figure 6:
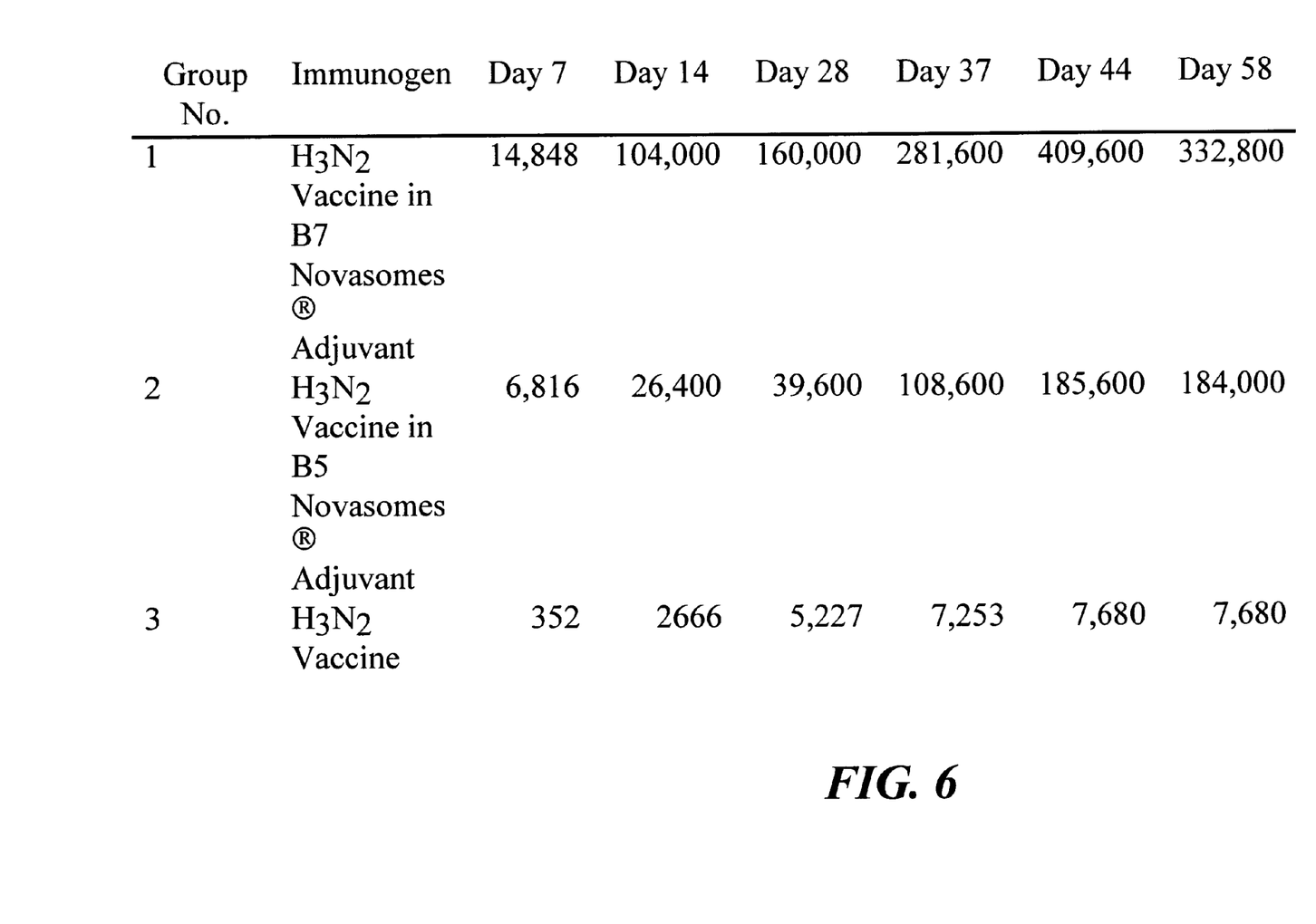
FIG. 6 illustrates anti-$H_3N_2$ serum IgG titers for rats at Days 7, 14, 28, 37, 44 and 58 following two inoculations with adjuvanted influenza vaccine and a non-adjuvanted influenza vaccine.
Figure 7:
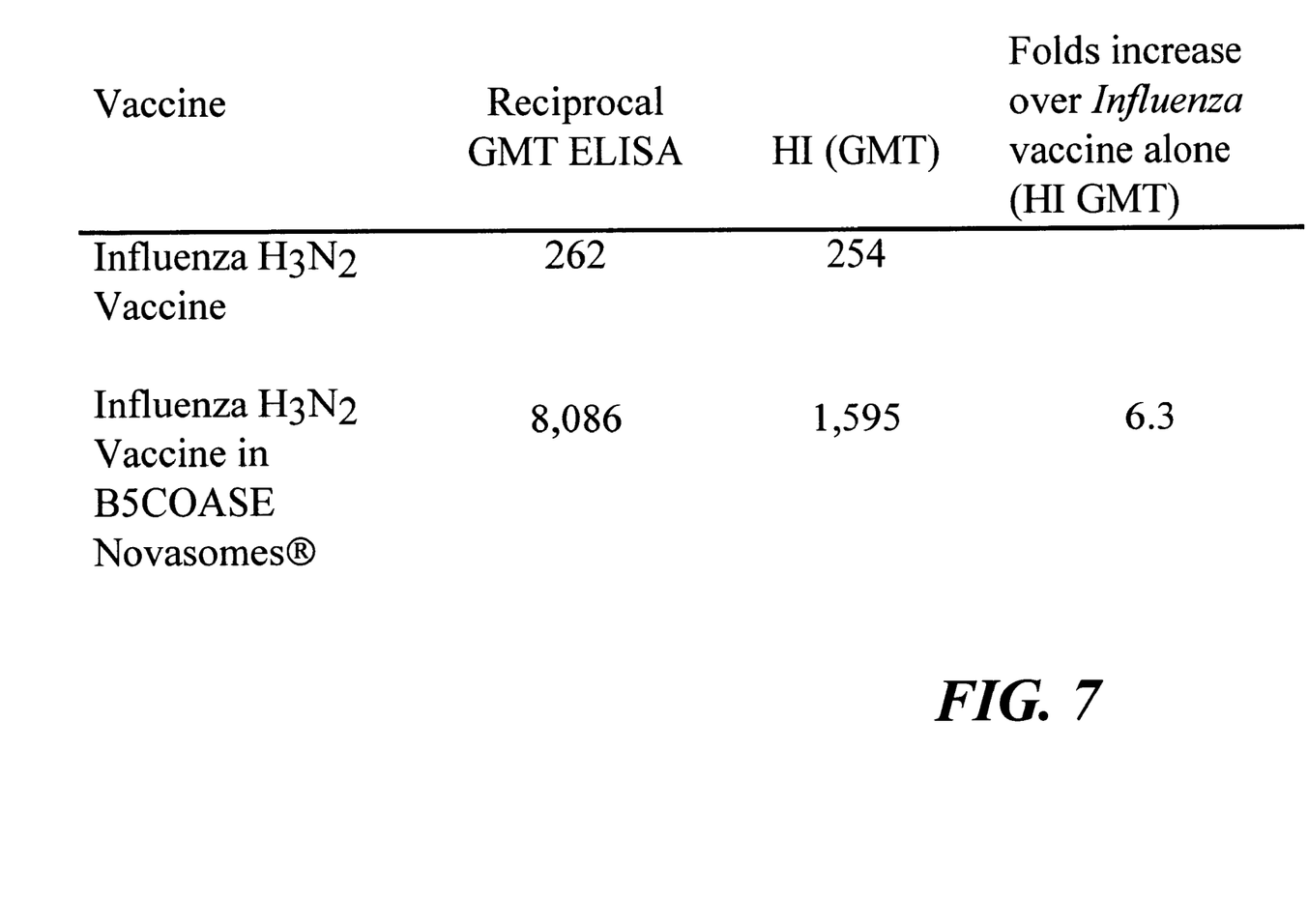
FIG. 7 illustrates the Hemagglutination Inhibition (HIA) and Enzyme-Linked Immunosorbent Assay (ELISA) results in rats at Day 65 following two inoculations with each of an adjuvanted influenza vaccine and a non-adjuvanted influenza vaccine.

An adjuvanted vaccine containing the antigen influenza A $H_3N_2$ (Beijing) was prepared using nonphospholipid paucilamellar lipid vesicles as adjuvants. Adjuvanticity of the two formulations, namely, non-specific immune stimulator and carrier adjuvant formulations was compared using the mean IFA of each composition, as compared with that of the antigen alone, as shown in FIG. 1.

Adjuvant formulations were prepared using an automated syringe machine, specifically a 5cc syringe machine. The adjuvant could also be made according to the general procedure set forth in U.S. Pat. No. 4,911,928. Briefly, the lipid components of the vesicle walls were heated to a flowable state and placed in a first component of the syringe machine. The aqueous component, in this case containing the antigen Fluzone™ (see below), was heated and placed in a second component of the syringe machine. The materials were then mixed using shear mixing until vesicles formed, encapsulating the antigen in the central cavity. However, in this and the following Examples, any method of achieving the proper shear could be used, including the manual techniques described in U.S. Pat. No. 4,911,928 (two syringes connected via a stopcock), or a flow device such as the NOVAMIX vesicle former. The basic details of the NOVA-MIX system are described in U.S. Pat. No. 4,895,452, the disclosure of which is incorporated herein by reference.

The antigen used in this example was FLUZONE a formalin-inactivated detergent-extracted influenza vaccine from Connaught. The formulation for the adjuvants used in this Example are set forth in Tables 1 and 2 below

TABLE 1

| | |
|---|---|
| Lipid Formulation | Brij 52 (7.0 g); cholesterol (2.69 g) |
| Diluent | Water for injection (WFI) containing 2.4 μg/ml Fluzone |
| Diluent Volume | 4.0 mL |
| Charge | Negative (Oleic acid 0.31 g) |
| Oil | Squalene |
| Hydration Ratio | 1.6/1 (lipid/squalene) 1.0/4.0 (lipid, oil/Diluent) |
| Temperature of WFI Phase | 60° C. |
| Temperature of Lipid Phase | 85° C. |
| pH | 5.85 |
| Final Volume | 5 ml |

For the first vaccine preparation, where the adjuvant encapsulates the antigen, the vaccine was made according to the formula of Table 1. The second vaccine preparation is made according to the formula of Table 2 below, where the diluent is water, without the antigen.

TABLE 2

| | |
|---|---|
| Lipid Formulation | Brij 52 (7.0 g); cholesterol (2.69 g) |
| WFI | Water for injection (WFI) |
| Diluent Volume | 4.0 mL |
| Charge | Negative (Oleic acid 0.31 g) |
| Oil | Squalene |
| Hydration Ratio | 1.6/1 (lipid/squalene) 1.0/4.0 (lipid, oil/Diluent) |
| Temperature of WFI Phase | 60° C. |
| Temperature of Lipid Phase | 85° C. |
| pH | 5.85 |
| Final Volume | 5 ml |

The adjuvant for the third vaccine preparation is prepared according to the method described above and then diluted 1:10. Of that diluted adjuvant, 100 μl are added to 2.4 μl of the FLUZONE™ antigen for injection into each animal.

Three groups of ten $C_3H$ seven week old female mice were injected with each vaccine preparation, resulting in 2.4 μg of antigen given per mouse. The first group of mice received one injection of the antigen alone; the second group received one injection of the antigen incorporated into the adjuvant; and the third group of mice received one injection of the antigen intermixed with the one to ten dilution of adjuvant. As can be seen from FIG. 1, which illustrates mean IFA results at Day 42, the adjuvanted vaccines improved the antigenic response significantly over the antigen alone. The adjuvant encapsulating the antigen exhibits a 10-fold increase over the antigen alone, and the diluted adjuvant exhibits a 7 fold increase.

Example 2

In this example, New Zealand Albino rabbits from Hazelton Labs were immunized with adjuvanted influenza A (Beijing) $H_3N_2$ vaccines to compare the adjuvant formulations of the present invention with the antigen alone, and with two other adjuvants not suitable for use in humans.

Each group of six rabbits (three males and three females) was injected with 9.8 μg of influenza A $H_3N_2$ antigen per animal. This antigen is a whole virus preparation produced in chicken eggs, which has been formalin-inactivated and purified by centrifugation and column filtration. In each case, 0.5 ml of the vaccine was injected intramuscularly into each rabbit at Days 0 and 14. The data from FIGS. 2 and 3 was determined from a bleeding taken on Day 27.

The first group of rabbits received the antigen alone, the second group of rabbits received the antigen adjuvanted with 16 μg alum/1 μg protein (Resorptar Armour Pharmaceuticals). The third group received the antigen adjuvanted with a 1:1 mixture (vol/vol) incomplete Freund's (Sigma Chemical).

The fourth group of rabbits received the antigen encapsulated in paucilamellar lipid vesicles prepared according to the formula set out in Table 3 below, prepared as described in Example 1, and the fifth group received 9.8 μg antigen in solution 1:1 (vol/vol) with adjuvant, specifically the paucilamellar lipid vesicles prepared according to the formulation set forth in Table 4 below.

TABLE 3

| | |
|---|---|
| Lipid Formulation | Brij 52 (17.5 g), cholesterol (6.4 g) |
| Diluent | Water for injection (WFI) with 9.8 μg antigen |
| Diluent Volume | 3.7 mL |
| Charge | None |
| Oil | Soybean oil |
| Hydration Ratio | (1.4 ml lipid/1 ml oil);<br>1.3/3.7 (lipid/oil to WFI) |
| Temperature of WFI Phase | 56° C. |
| Temperature of Lipid Phase | 74° C. |
| pH | 6.6 |
| Final Volume | 5 ml |

TABLE 4

| | |
|---|---|
| Lipid Formulation | Brij 52 (17.5 g), cholesterol (6.4 g) |
| Diluent | Water for injection (WFI) |
| Diluent Volume | 3.7 mL |
| Charge | None |
| Oil | Soybean oil |
| Hydration Ratio | (1.4 mL lipid/1 mL oil);<br>1.3/3.7 (lipid/oil to WFI) |
| Temperature of WFI Phase | 56° C. |
| Temperature of Lipid Phase | 74° C. |
| pH | 6.6 |
| Final Volume | 5 mL |

As can be seen from FIGS. 2 and 3, the adjuvanted vaccine according to the present invention has equivalent or increased antibody response and antigenicity when compared with that of known adjuvants. The mean IFA results were calculated as described above. The mean HI values, were obtained from testing with chicken red blood cells, as is known in the art, the results of which correlate with protection capabilities of the vaccine.

Example 3

In this Example, certain Sprague-Dawley rats from Charles River Labs were immunized with an influenza A/Beijing 32/92 $H_3N_2$ subunit non-fusogenic NOVASOME vaccine, and others were immunized with an influenza A/Beij

TABLE 9

| | |
|---|---|
| Lipid Formulation | Brij 52 (17.5 g), cholesterol (6.4 g) |
| Diluent | Water for Injection (WFI) with 9.8 μg antigen |
| Diluent Volume | 3.7 mL |
| Charge | None |
| Oil | Soybean oil |
| Hydration Ratio | (1.4 mL lipid/1 mL oil); 1.3/3.7 (lipid/oil to WFI) |
| Temperature of WFI Phase | 56° C. |
| Temperature of Lipid Phase | 74° C. |
| pH | 6.6 |
| Final Volume | 5 ml |

The foregoing Examples are merely illustrative and those skilled in the art may be able to determine other materials and methods which accomplish the same result. Such other materials and methods are included within the scope of the following claims.

What is claimed is:

1. An adjuvanted influenza vaccine for producing an antigenic response to influenza, in vivo, in mammals, said vaccine comprising:

an effective amount of an influenza antigen and an adjuvant, said adjuvant comprising oil-containing paucilamellar lipid vesicles having nonphospholipid materials as the primary wall forming constituent, wherein said paucilamellar lipid vesicles have 2–10 bilayers surrounding an amorphous central cavity, and wherein said nonphospholipid materials are selected from the group consisting of polyoxyethylene fatty acid esters, polyoxyethylene fatty acid ethers, polyoxyethylene sorbitan esters, polyoxyethylene glyceryl mono- and diesters, glyceryl mono- and distearate, sucrose distearate, propylene glycol stearate, long chain acyl hexosamides, long chain acyl amino acid amides, long chain acyl amides, glyceryl mono-and diesters, dimethyl acyl amines, $C_{12}$–$C_{20}$ fatty alcohols, $C_{12}$–$C_{20}$ glycol monoesters, and $C_{12}$–$C_{20}$ fatty acids, and wherein said vaccine increases the antigenic response when compared to the antigen alone or the antigen adjuvanted with alum, wherein the antigen is mixed in solution with the adjuvant.

2. The vaccine of claim 1 wherein said antigen is encapsulated in said adjuvant.

3. The vaccine of claim 1 wherein said antigen is encapsulated in said amorphous central cavity.

4. The vaccine of claim 1 wherein said antigen is selected from the group consisting of antigens derived from formalin-inactivated whole virus, antigens derived from formalin-inactivated viral subunits, and antigens produced by recombinant DNA techniques.

5. The vaccine of claim 4 wherein said antigen is influenza A $H_3N_2$.

6. The vaccine of claim 1 wherein said paucilamellar lipid vesicles further comprise at least one sterol selected from the group consisting of cholesterol, cholesterol derivatives, hydrocortisone, and phytosterol.

7. The vaccine of claim 1 wherein said paucilamellar lipid vesicles comprise an amorphous central cavity containing a water immiscible oily material.

8. The vaccine of claim 7 wherein said water immiscible oily material is selected from the group consisting of soybean oil, squalene oil, squalane oil, sesame oil, olive oil, canola oil, corn oil, rapeseed oil, safflower oil, sunflower oil, fish oils, petrolatum, avocado oil, triglyceride oils and fats, flavor oils, and water insoluble vitamins.

\* \* \* \* \*

UNITED STATES PATENT AND TRADEMARK OFFICE
CERTIFICATE OF CORRECTION

PATENT NO.     : 6,387,373 B1
DATED          : May 14, 2002
INVENTOR(S)    : D. Craig Wright and Donald F.H. Wallach It is certified that error appears in the above-identified patent and that said Letters Patent is hereby corrected as shown below:

<u>Title page, Item [54] and Column 1, line 1,</u>
"PAUCILSMELLAR" should read -- PAUCILAMELLAR --

<u>Column 4,</u>
Lines 5 and 8, after "Assay" insert -- (IFA) --
Lines 6 and 12, delete first occurrence of "DAY"
Line 12, after "Assay" insert -- (HIA") --
Lines 14 and 18, after "Assay" insert -- (HIA) and --
Lines 15 and 19, after "Immunsorbent" delete "and" and insert -- Assay (ELISA) --
Line 52, replace "filing" with -- fusing --

<u>Column 5,</u>
Line 62, replace "2.4 µL" with -- 2.4 µG -- and

<u>Column 7,</u>
Line 11, replace "H3N$_2$" with -- H$_3$N$_2$ --

Signed and Sealed this

Sixth Day of May, 2003

JAMES E. ROGAN
*Director of the United States Patent and Trademark Office*